United States Patent [19]
Bittman et al.

[11] Patent Number: 5,756,774
[45] Date of Patent: May 26, 1998

[54] SYNTHESIS OF MYO-INOSITOL PHOSPHATES

[76] Inventors: Robert Bittman, 1 Corncrib La., Roslyn Heights, N.Y. 11577; Lawrence Leung, 144-67 41st Ave., Flushing, N.Y. 11355

[21] Appl. No.: 794,957

[22] Filed: Feb. 4, 1997

[51] Int. Cl.$^6$ .................. C07D 317/70; C07F 9/02
[52] U.S. Cl. .................. 549/433; 558/161; 568/833
[58] Field of Search ................ 558/161, 156; 568/833; 536/44; 5493/458, 433

[56] References Cited

U.S. PATENT DOCUMENTS

| | | | |
|---|---|---|---|
| 4,873,355 | 10/1989 | Hobbs | 558/161 |
| 5,260,472 | 11/1993 | Chen | 558/161 |

OTHER PUBLICATIONS

Aguilo, A. et al., The Regioselective Synthesis of Enantiomerically Pure myo–inositol derivatives. Efficient Synthesis of myo–inositol 1,4,5–trisphosphate. Tetrahedron Lett vol. 33, pp. 401–404, 1992.

de la Prada et al., Improved Preparation of acetals of myo–inositol and its (±)—1—(±)-1—benzyl ether;—Carbohydrates Research vol. 207, pp. 249–257, 1990.

*Primary Examiner*—C. Warren Ivy
*Assistant Examiner*—Charanjit S. Aulakh
*Attorney, Agent, or Firm*—Kenneth B. Rubin

[57] ABSTRACT

Provided herein are novel syntheses of the phosphate-based inositol derivatives 1-O-[(+)-menthoxycarbonyl]-6-O-benzyl-2,3:4,5-di-O-isopropylidene-myo-inositol (D4P), D-myo-inositol 1,4,5-trisphosphate (D-IP$_3$), 6-O-benzyl-2,3:4,5-di-O-isopropylidene-myo-inositol H-phosphonate ((−)-3-HP) and L-myo-inositol 1,4,5-trisphosphate (L-IP$_3$). These syntheses employ fewer column chromatography steps for the isolation of intermediates than do prior art syntheses, and hence, are more convenient, economical and efficient than are the previously known synthetic methods.

23 Claims, No Drawings

SYNTHESIS OF MYO-INOSITOL PHOSPHATES

FIELD OF THE INVENTION

This invention is directed to the synthesis of phosphate-based inositol derivatives by rapid, economic and efficient processes.

BACKGROUND OF THE INVENTION

Many signaling molecules, such as hormones and neurotransmitters, exert effects on their target cell by binding to a receptor in the cell's membranes. Following binding, presence of the signaling molecule on its receptor is translated into an effect within the target cell by one or more molecules located within the membrane. The compound responsible for transducing the effect of many signaling molecules is believed to be phosphatidylinositol 4,5-bisphosphate ("PIP$_2$").

Hydrolysis of PIP$_2$, following binding of a signalling molecule to its receptor, results in the formation of D-myo-inositol 1,4,5-trisphosphate ("D-IP$_3$") and diacylglycerol. D-IP$_3$ causes calcium to be released from intracellular, nonmitochondrial stores; increased intracellular calcium levels, in turn, result in a variety of responses within the cell, such as muscle contraction, cell aggregation and thromboxane B$_2$ release. Moreover, diacylglycerol, together with phosphatidylserine and calcium, activates protein kinase C. PKC is well known to phosphorylate a number of proteins involved in the regulation of cell metabolism.

Accordingly, D-IP$_3$ and other phosphate-based inositol derivatives are useful in a variety of ways, including elucidative study of the pathways and mecahnisms by which external signals affect intracellular processes. For example, isolation and identification of intracellular D-IP$_3$ receptors is helpful in illuminating the role of calcium mobilization in various physiological and pathological processes, as well as for the development of pharmacological agents capable of modulating the effects of calcium mobilization.

Synthesis of D-IP$_3$ has previously been reported (see S. Ozaki et al., 1986). However, Ozaki's process requires separation of several inositol diastereomers by column chromatography, a costly, inefficient and commercially impracticable process requiring silica gel that costs about $150/kilogram. Although others (see J. Gigg et al., 1985; R. de la Pradilla et al., 1990; N. Noda et al., 1990; Chen et al., U.S. Pat. No. 5,260,472) have reported D-IP$_3$ synthesis via fewer intermediates than arise in Ozaki's process, their methods still require multiple chromatographic separations, and/or reactants that are not commercially available.

This invention provides rapid, convenient and economical synthesis of the enantiomerically pure inositol derivatives D-IP$_3$ and L-IP$_3$, employing minimal use of chromatography. Reaction intermediates are generally isolated by crystallization, and the reagents used are all commercially available, at relatively low cost.

Moreover, one of the intermediates made during the synthetic process can be converted into a useful precursor for the synthesis of inositol-based lipids and inositol analogs. The inositol-H-phosphonate (−)-3-HP provided can be used to prepare various phosphatidylinositols.

SUMMARY OF THE INVENTION

This invention provides rapid, convenient and economical synthesis of 1-O-[(+)-menthoxycarbonyl]-6-O-benzyl-2,3,4,5-di-O-isopropylidene-myo-inositol ("D4P"), D-myo-inositol 1,4,5-trisphosphate ("D-iP$_3$"), inositol 6-O-benzyl-2,3:4,5-di-O-isopropylidene-myo-inositol H-phosphonate ("(−)-3-HP") and L-myo-inositol 1,4,5-trisphosphate ("L-iP$_3$"). The syntheses require fewer chromatographic isolation steps than do previously known reaction schemes.

D4P is synthesized according to the practice of this invention from D-myo-inositol via the intermediates (±)-2, 3:4,5-di-O-isopropylidene-myo-inositol ("(±)-2"), (±)-6-O-benzyl-2,3:4,5-di-O-isopropylidene ("(±)-3") and 1-O-[(+)-menthoxycarbonyl]-6-O-benzyl-2,3:4,5-di-O-isopropylidene-myo-inositol ("4P"), following which D4P is isolated from the racemic 4P by crystallization with methanol. D-IP$_3$ is made from D4P via the intermediates (+)-6-O-benzyl-2,3-O-isopropylidene myoinositol and 6-O-benzyl-2,3-O-isopropylidene-myo-inositol 1,4,5-tris (dibenzyl phosphate). Chromatography is employed during this synthesis only for the isolation of 6-O-benzyl-2,3-O-isopropylidene-myo-inositol 1,4,5-tris(dibenzyl phosphate).

(−)-3-HP is made from D-4P via the intermediate (−)-6-O-benzyl-2,3-O-isopropylidene-myo-inositol. L-IP$_3$ is made via the compounds (±)-6-O-benzyl-2,3:4,5-di-O-isopropylidene-myo-inositol ((±)-3), 3-O-[(+)-menthoxycarbonyl]-4-O-benzyl-1,2:5,6-di-O-isopropylidene-myo-inositol (4M), 4-O-benzyl-1,2-O-isopropylidene-myoinositol 3,5,6-tris(dibenzyl phosphate) and 4-O-benzyl-1,2-O-isopropylidene-myo-inositol 3,5,6-tris(dibenzyl phosphate). Chromatography is exployed during this synthesis only for the isolation of 4-O-benzyl-1,2-O-isopropylidene-myo-inositol 3,5,6-tris(dibenzyl phosphate).

DETAILED DESCRIPTION OF THE INVENTION

Following are abbreviations, and the full names of chemical compounds designated by the abbreviations, which may be found in this application: 1-O-[(+)-menthoxycarbonyl]-6-O-benzyl-2,3:4,5-di-O-isopropylidene-myo-inositol: D4P; (±)-2,3:4,5-di-O-isopropylidene-myo-inositol: (±)-2; (±)-6-O-benzyl-2,3:4,5-di-O-isopropylidene-myo-inositol: (±)-3; rac-1-O-[(+-menthoxycarbonyl]-6-O-benzyl-2,3:4,5-di-O-isopropylidene-myo-inositol: 4P; D-myo-inositol 1,4, 5-trisphosphate: D-IP$_3$; m-chloroperoxybenzoic acid: mCPBA; inositol 6-O-benzyl-2,3:4,5-di-O-isopropylidene-myoinositol H-phosphonate: (−)-3-HP; L-myo-inositol 1,4, 5-trisphosphate: L-IP$_3$; and, 3-O-[(+)-menthoxycarbonyl]-4-O-benzyl-1,2:5,6-di-O-isopropylidene-myo-inositol: 4M.

This invention provides in general the synthesis of phosphoinositol derivatives, using H-phosphonates as intermediates and (+)-menthyl chloroformate to separate the various inositol derivatives. More specifically, a method is described of preparing D-1-O-[(+)-menthoxycarbonyl]-6-O-benzyl-2,3:4,5-di-O-isopropylidene-myoinositol ("D-4P") (see scheme 1, hereinbelow). Also provided herein is a method of preparing enantiomerically pure D-myo-inositol 1,4,5-trisphosphate ("D-IP$_3$") (see scheme 1, hereinbelow).

The first step in the process of preparing D-4P involves conversion of my inositol to (±)-2,3:4,5-di-O-isopropylidene-myo-inositol ("(±)-2") by acetonation of myo-inositol so as to give (±)-2,3-O-isopropylidene-myo-inositol, and acetonation of this product so as to give (±)-2,3:4,5-di-O-isopropylidene-myo-inositol. Next, this (±)-2 is converted to (±)-6-O-benzyl-2,3:4,5-di-O-isopropylidene ("(±)-3)") by stannylation of (±)-2,3:4,5-di-O-isopropylidene-myo-inositol, followed by benzylation of this product so as to give (±)-6-benzyl-2,3:4,5-di-O-isopropylidene. Benzylation is accomplished by a number of means well known to ordinarily skilled artisans including, without limitation: reaction using cesium fluoride in benzyl bromide; sonication with silver oxide in benzyl bromide; phase transfer catalysis using sodium hydroxide in benzyl bromide; and, reaction with thallous ethoxide in benzyl bromide. Preferably, benzylation is by reaction with cesium fluoride and benzyl bromide.

(±)-3 is then converted to rac-1-O-[(+)-menthoxycarbonyl]-6-O-benzyl-2,3:4,5-di-O-isopropylidene-myoinositol ("4P"), for example, by acylation of (±)-3 with menthyl chloroformate. D-4P is isolated from the racemate 4-P product, for example, using methanol. Proton and phosphorous NMR spectra of these compounds, as well as the other compounds made herein, have been conducted by standard means and are consistent with the predicted structures (for the spectra of the compound (±)-3, see Chung and Ryu, 1994)).

The first step in the process of preparing enantiomerically pure D-myo-inositol 1,4,5-trisphosphate ("D-IP$_3$") (see scheme 1, hereinbelow) involves conversion of (+)-6-O-benzyl-2,3-O-isopropylidene-myo-inositol by hydrolysis of the D4P, e.g., with pyridinium p-toluenesulfonate, so as to give 1-O-[(+)-menthoxycarbonyl]-6-O-benzyl-2,3-O-isopropylidene-myo-inositol. This product is subjected to alkaline hydrolysis so as to give (+)-6-O-benzyl-2,3-O-isopropylidene-myoinositol. The product of this step is then converted to 6-O-benzyl-2,3-O-isopropylidene-myo-inositol 1,4,5-tris(dibenzyl phosphate) by first phosphorylating (+)-6-O-benzyl-2,3-O-isopropylidene-myo-inositol so as to give 6-O-benzyl-2,3-O-isopropylidene-myo-inositol 1,4,5-tris(dibenzyl phosphite). Phosphorylation can be by any means generally accepted in the art for attaching phosphorous atoms to compounds; preferably, this phosphorylation step is conducted with N,N-diisopropyl-di-benzyl phosphoramidite.

Following phosphorylation, the phosphite is oxidized in situ, e.g., with m-chloroperoxybenzoic acid ("mCPBA"), so as to give 6-O-benzyl-2,3-O-isopropylidene-myo-inositol 1,4,5-tris(dibenzyl phosphate). 6-O-Benzyl-2,3-O-isopropylidene-myo-inositol 1,4,5-tris(dibenzyl phosphate) is isolated from the resulting phosphate, for example, using SiO$_2$ chromatography. D-IP$_3$ is then formed by hydrogenolysis of 6-O-benzyl-2,3-O-isopropylidene-myo-inositol 1,4,5-tris(dibenzyl phosphate), for example, using palladium on charcoal, so as to give 2,3-O-isopropylidene-myo-inositol 1,4,5-trisphosphate. Acidification of this product, e.g., with acetic acid, gives D-myo-inositol 1,4,5-trisphosphate.

Further provided herein is a method of preparing 6-O-benzyl-2,3:4,5-di-O-isopropylidene-myoinositol H-phosphonate ("(−)-3-HP") (see scheme 2, hereinbelow). This method involves hydrolysis of D4P with potassium carbonate in methanol so as to give (−)-6-O-benzyl-2,3-O-isopropylidene-myo-inositol ("(−)-3"), followed by conversion of the product to (−)-3-HP using PCl$_3$ and imidazole.

Still further provided herein is a method of preparing enantiomerically pure L-myo-inositol 1,4,5-trisphosphate (L-IP$_3$) (see scheme 3 hereinbelow). First, (±)-6-O-benzyl-2,3:4,5-di-O-isopropylidene ("(±)-3") is converted to rac-3-o-[(−)-menthoxycarbonyl]-4-O-benzyl-1,2:5,6-di-O-isopropylidene-myoinositol ("4M"), preferably, but not necessarily, by acylation with (−)-menthyl chloroformate. L4M is crystallized from the product of this reaction, e.g., with methanol. It is then converted to 4-O-benzyl-1,2-O-isopropylidene-myoinositol 3,5,6-tris(dibenzyl phosphate) by phosphitylation of 4-O-benzyl-1,2-isopropylidene-myoinositol, e.g., with N,N-diisopropyl-dibenzyl phosphoramidite so as to give 4-O-benzyl-1,2-O-isopropylidene-myo-inositol 3,5,6-tris(dibenzyl phosphite). In situ oxidation of the product, e.g., with m-chloroperoxybenzoic acid, gives 4-O-benzyl-1,2-O-isopropylidene-myo-inositol 3,5,6-tris(dibenzyl phosphate), which is then isolated by a number of means, including SiO$_2$ chromatography. L-myo-inositol 1,4,5-trisphosphate is then formed by hydrogenolysis of 4-O-benzyl-1,2-O-isopropylidene-myo-inositol 3,5,6-tris(dibenzyl phosphate), e.g., using palladium on charcoal, so as to give 1,2-O-isopropylidene-myo-inositol 3,5,6-trisphosphate. This product is then acidified with acetic acid so as to give L-myo-inositol 3,5,6-trisphosphate.

This invention will be better understood from the following examples. However, those of ordinary skill in the art will readily understand that the examples are merely illustrative of the invention as defined in the claims which follow thereafter. The description given herein includes such modifications to its compounds, reactants, reaction schemes and other provisions, that are obvious to ordinarily skilled artisans given the teachings of this invention.

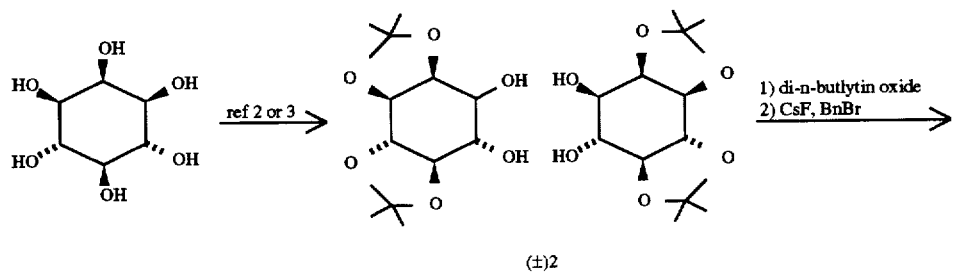

(±)2

-continued
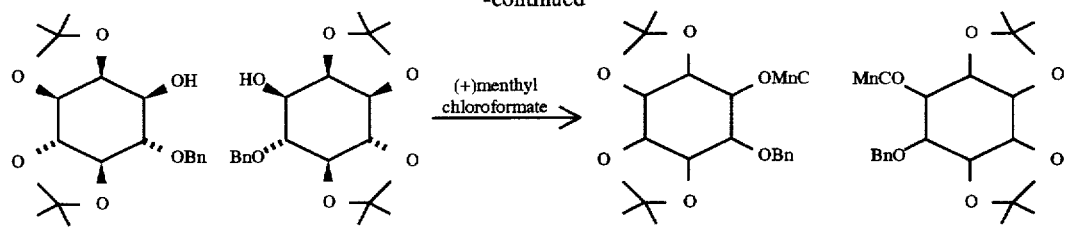
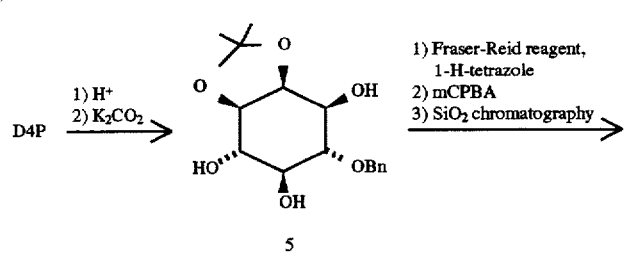
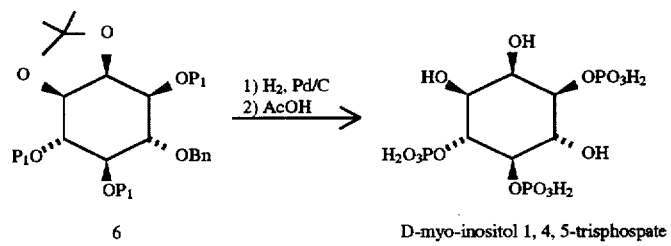
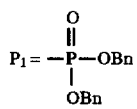
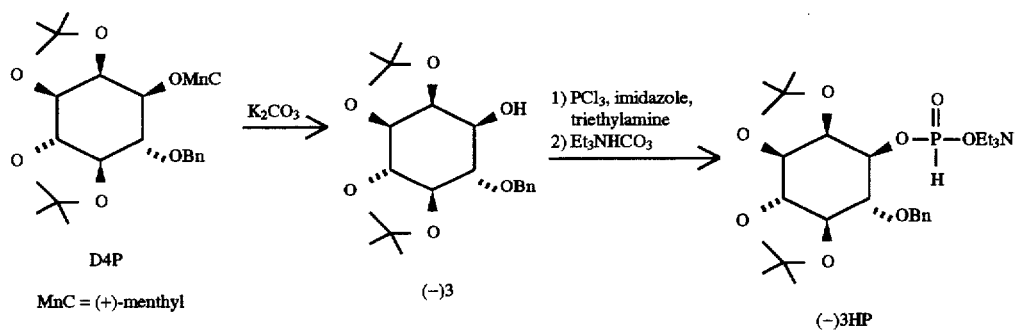
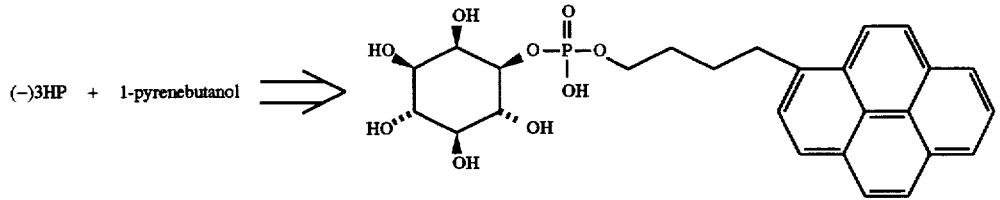

EXAMPLES

Example 1

Chromatography

All flash and $SiO_2$ chromatography was conducted using Kieselgel™ 60 (EM Science). All compounds made were judged to be pure using thin layer chromatography (Kieselgel™ 60, impregnated on aluminum sheets).

Example 2

Synthesis of D4P

Myo-inositol was converted (see scheme 1) to (±)-2,3:4,5-di-O-isopropylidene-myo-inositol according to the methods of Gigg et al. or de la Pradilla et al. (the contents of which are incorporated herein by reference). Regioselective monobenzylation of (±)-2 was accomplished via an O-stannylated intermediate to give (±)-6-O-benzyl-2,3:4,5-di-O-isopropylidene-myo-inositol ("(±)-3"), readily purified by flash chromatography (hexane:ethyl acetate 4:1), in 60% yield. (±)-3 was converted to racemic 4P using (+)-menthyl chloroformate.

D4P (mp 128°–131° C.) was isolated from the racemic 4P by recrystallization in methanol.

Example 3

Synthesis of D-IP$_3$

Selective hydrolysis of the transketal of D4P (see scheme 1) with pyridinium p-toluenesulfonate, followed by alkaline hydrolysis of the menthyl carbonate in methanol, gave the triol (+)-6-O-benzyl-2,3-O-isopropylidene-myo-inositol (5, $[\alpha]^D_{24° C.}$ +21° (c 0.43, (CHCl$_2$); lit (de la Pradilla et al.) $[\alpha]^D$+15° (c 0.6, CH$_3$OH)) in 40% yield after purification by flash chromatography. The triol was also crystallized in 32% yield from the crude reaction mixture using hexane:ethyl acetate (4:1). Phosphitylation of the triol with N,N-diisopropyldibenzyl phosphoramidite (Fraser-Reid reagent), followed by in situ oxidation with mCPBA, gave 6-O-benzyl-2,3-O-isopropylidene-myo-inositol in 92% yield, after purification by flash chromatography. Hydrogenolysis gave 6-O-benzyl-2,3-O-isopropylidene-myo-inositol over palladium on charcoal, followed by acidification with acetic acid, gave D-IP$_3$ in quantitative yield ($[\alpha]^D_{24° C.}$ −20° (c 0.05, H$_2$O, pH 9); lit. (Liu et al.); ($[\alpha]^D$−30° (c 0.5, H$_2$O, pH 9.5)).

Example 4

Synthesis of L-IP$_3$

Reaction of (±)-3, prepared as described in Example 1 hereinabove, with (−)-menthyl chloroformate (see scheme 2), followed by crystallization with methanol, gave enantiomerically pure L4M (mp 130°–131° C.), the enantiomer of D4P. Following the same scheme as set forth in Example 3 hereinabove, but using L4M as the starting material instead of D4P (see scheme 2), gave L-IP$_3$ in similar yield (($[\alpha]^D_{24° C.}$ +17° (c 0.30, H$_2$O,pH 10)).

Example 5

Synthesis of (−)-3-HP

Hydrolysis of D4P with potassium carbonate (see scheme 3) in methanol gave (−)-3($[\alpha]^D_{24° C.}$−17.4° (c 1.69, CHCl$_3$); lit. (Chen et al.): ($[\alpha]^D$−16° (c 0.9, CHCl$_3$)) in quantitative yield after column chromatography (hexane:ethyl acetate 4:1). Conversion to the corresponding H-phosphonate with PCl$_3$ and imidazole gave the product (−)-3-HP in 70% yield. (−)-3-HP was a colorless liquid that was stable for several months at −20° C.

What is claimed is:

1. A method of preparing 1-O-[(+)-menthoxycarbonyl]-6-O-benzyl-2,3:4,5-di-O-isopropylidene-myo-inositol which comprises:
    (a) converting D-myo-inositol to (±)-2,3:4,5-di-O-isopropylidene-myo-inositol by the steps of:
        (i) acetonation of myo-inositol so as to give (±)-2,3-O-isopropylidene-myo-inositol; and,
        (ii) acetonation of the product of step (i) so as to give to (±)-2,3:4,5-di-O-isopropylidene-myo-inositol;
    (b) converting the product of step (a) to (±)-O-6-benzyl-2,3:4,5-di-O-isopropylidene by the steps of:
        (i) stannylation of (±)-2,3:4,5-di-O-isopropylidene-myo-inositol; and,
        (ii) benzylation of the product of step (i) so as to give (±)-6-O-benzyl-2,3:4,5-di-O-isopropylidene myo-inositol;
    (c) converting the product of step (b) to 1-O-[(+)-menthoxycarbonyl]-6-O-benzyl-2,3:4,5-di-O-isopropylidene-myoinositol; and,
    (d) isolation of 1-O-[(+)-menthoxycarbonyl]-6-O-benzyl-2,3:4,5-di-O-isopropylidene-myo-inositol from the product of step (c).

2. The method of claim 1, wherein the benzylation of step (b)(ii) is by reaction with cesium fluoride and benzyl bromide.

3. The method of claim 1, wherein the conversion of step (c) is by acylation with (+)-menthyl chloroformate.

4. The method of claim 1, wherein 1-O-[(+)-menthoxycarbonyl]-6-O-benzyl-2,3:4,5-di-O-isopropylidene-myoinositol is recrystallized in step (d) with methanol.

5. A method of preparing 6-O-benzyl-2,3:4,5-di-O-isopropylidene-myo-inositol H-phosphonate which comprises the steps of:
    (a) hydrolysis of the 1-O-[(+)-menthoxycarbonyl]-6-O-benzyl-2,3:4,5-di-O-isopropylidene-myo-inositol of claim 1 so as to give (−)-6-O-benzyl-2,3:4,5-O-isopropylidene-myo-inositol; and,
    (b) converting the product of step (a) to 6-O-benzyl-2,3:4,5-di-O-isopropylidene-myo-inositol H-phosphonate by reaction with PCl$_3$ and imidazole.

6. The method of claim 5, wherein the hydrolysis of step (a) is with potassium carbonate in methanol.

7. The method of claim 5, wherein (−)-6-O-benzyl-2,3:4,5-O-isopropylidene-myo-inositol is converted by reaction with PCl$_3$ and imidazole.

8. A method of preparing enantiomerically pure D-myo-inositol 1,4,5-trisphosphate which comprises:
    (a) converting D-myo-inositol to (±)-2,3:4,5-di-O-isopropylidene-myo-inositol by the steps of:
        (i) acetonation of myo-inositol so as to give (±)-2,3-O-isopropylidene-myo-inositol; and,
        (ii) acetonation of the product of step (i) so as to give to (+)-2,3:4,5-di-O-isopropylidene-myoinositol;
    (b) converting the product of step (a) to (±)-6-O-benzyl-2,3:4,5-di-O-isopropylidene by the steps of:
        (i) stannylation of (±)-2,3:4,5-di-O-isopropylidene-myoinositol; and, (ii) benzylation of the product of step (i) so as to give (±)-6-O-benzyl-2,3:4,5-di-O-isopropylidene myo-inositol;
    (c) converting the product of step (b) to 1-O-[(+)-menthoxycarbonyl]-6-O-benzyl-2,3:4,5-di-O-isopropylidene-myo-inositol;

(d) isolation of 1-O-[(+)-menthoxycarbonyl]-6-O-benzyl-2,3:4,5-di-O-isopropylidene-myo-inositol from the product of step (c);

(e) converting 1-O-[(+)-menthoxycarbonyl]-6-O-benzyl-2,3:4,5-di-O-isopropylidene-myo-inositol to (+)-6-O-benzyl-2,3-O-isopropylidene myo-inositol by the steps of:
  (i) hydrolysis of 1-O-[(+)-menthoxycarbonyl]-6-O-benzyl-2,3:4,5-di-O-isopropylidene-myo-inositol with pyridinium p-toluenesulfonate so as to give 1-O-[(+)-menthoxycarbonyl]-6-O-benzyl-2,3-O-isopropylidene-myo-inositol; and,
  (ii) alkaline hydrolysis of the product of step (i) so as to give (+)-6-O-benzyl-2,3-O-isopropylidene-myo-inositol;

(f) converting the product of step (e) to (−)-6-O-benzyl-2,3-O-isopropylidene-myo-inositol 1,4,5-tris(dibenzyl phosphate) by the steps of:
  (i) phosphitylation of the product of step (a) so as to give (−)-6-O-benzyl-2,3-O-isopropylidene-myo-inositol 1,4,5-tris(dibenzyl phosphite);
  (ii) in situ oxidation of the product of step (i) so as to give (−)-6-O-benzyl-2,3-O-isopropylidene-myo-inositol 1,4,5-tris(dibenzyl phosphate); and,
  (iii) isolation of (−)-6-O-benzyl-2,3-O-isopropylidene-myo-inositol 1,4,5-tris(dibenzyl phosphate) from the product of step (ii) using $SiO_2$ chromatography; and, (g) converting the product of step (f) to D-myo-inositol 1,4,5-trisphosphate by the steps of:
  (i) hydrogenolysis of the product of step (b) so as to give D-2,3-O-isopropylidene-myo-inositol 1,4,5-trisphosphate; and,
  (ii) acidification of the product of step (ii) so as to give D-myo-inositol 1,4,5-trisphosphate.

9. The method of claim 8, wherein the phosphorylation of step (f)(i) is by reaction with with N,N-diisopropyl-dibenzyl phosphoramidite.

10. The method of claim 8, wherein the in situ oxidation of step (f)(ii) is with m-chloroperoxybenzoic acid ("mCPBA").

11. The method of claim 8, wherein the hydrogenolysis of step (g)(i) is with palladium on charcoal.

12. The method of claim 8, wherein the acidification of step (g)(ii) is with acetic acid.

13. A method of preparing enantiomerically pure L-myo-inositol 1,4,5-trisphosphate which comprises the steps of:
  (a) hydrolysis of 1-O-[(+)-menthoxycarbonyl]-6-O-benzyl-2,3:4,5-di-O-isopropylidene-myo-inositol so as to give (−)-6-O-benzyl-2,3:4,5-O-isopropylidene-myo-inositol;
  (b) converting the product of step (a) to (±)6-O-benzyl-2,3:4,5-di-O-isopropylidene-myo-inositol H-phosphonate by reaction with $PCl_3$ and imidazole,
  (c) acylation of (±)-6-O-benzyl-2,3:4,5-di-O-isopropylidene with (−)-menthyl chloroformate so as to give 3-O-[(+)-menthoxycarbonyl]-4-O-benzyl-1,2:5,6-di-O-isopropylidene-myo-inositol;

(d) crystallization of 3-O-[(+)-menthoxycarbonyl]-4-O-benzyl-1,2:5,6-di-O-isopropylidene-myo-inositol from the product of step (c);

(e) converting 3-O-[(+)-menthoxycarbonyl]-4-O-benzyl-1,2:5,6-di-O-isopropylidene-myo-inositol to +-4-O-benzyl-1,2-O-isopropylidene-myo-inositol 3,5,6-tris(dibenzyl phosphate) by the steps of:
  (i) phosphitylation of 3-O-[(+)-menthoxycarbonyl]-4-O-benzyl-1,2:5,6-di-O-isopropylidene-myo-inositol so as to give 4-O-benzyl-1,2-O-isopropylidene-myo-inositol 3,5,6-tris(dibenzyl phosphite); and,
  (ii) in situ oxidation of the product of step (i) so as to give +-4-O-benzyl-1,2-O-isopropylidene-myo-inositol 3,5,6-tris(dibenzyl phosphate);

(f) isolation of +-4-O-benzyl-1,2-O-isopropylidene-myo-inositol 3,5,6-tris(dibenzyl phosphate) from the product of step (e);

(g) hydrogenolysis of +-4-O-benzyl-1,2-O-isopropylidene-myo-inositol 3,5,6-tris(dibenzyl phosphate) so as to give L-1,2-O-isopropylidene-myo-inositol 3,5,6-trisphosphate; and, (h) acidification of L-1,2-O-isopropylidene-myo-inositol 3,5,6-trisphosphate so as to give L-myo-inositol 3,5,6-trisphosphate.

14. The method of claim 13, wherein 3-O-[(+)-menthoxycarbonyl-4-O-benzyl-1,2:5,6-di-O-isopropylidene-myo inositol is recrystallized in step (b) using methanol.

15. The method of claim 13, wherein the phosphitylation of step (c)(i) is with N,N-diisopropyl-dibenzyl phosphoramidite.

16. The method of claim 13, wherein the in situ oxidation of step (c)(ii) is with m-chloroperoxybenzoic acid.

17. The method of claim 13, wherein 4-O-benzyl-1,2-O-isopropylidene-myo-inositol 3,5,6-tris(dibenzyl phosphate) is isolated in step (d) is using $SiO_2$ chromatography.

18. The method of claim 13, wherein the hydrogenolysis of strep (d) is using palladium on charcoal.

19. The method of claim 13, wherein the acidification of step (f) is with acetic acid.

20. The method of claim 13, wherein the hydrolysis of step (a) is with potassium carbonate in methanol.

21. The method of claim 8, wherein the benzylation of step (b)(ii) is by reaction with cesium fluoride and benzyl bromide.

22. The method of claim 8, wherein the conversion of step (c) is by acylation with (+)-menthyl chloroformate.

23. The method of claim 8, wherein 1-O-[(+)-menthoxycarbonyl]-6-O-benzyl-2,3:4,5-di-O-isopropylidene-myo-inositol is recrystallized in step (d) with methanol.

* * * * *